United States Patent [19]

Cooper et al.

[11] 4,410,634
[45] Oct. 18, 1983

[54] METHOD OF PASSIVELY ADSORBING IMMUNO-REACTIVE HAPTENS TO SOLID PHASES

[75] Inventors: Harold R. Cooper; Andrew O'Beirne, both of Walkersville, Md.

[73] Assignee: Dynasciences Corporation, Los Angeles, Calif.

[21] Appl. No.: 320,919

[22] Filed: Nov. 12, 1981

Related U.S. Application Data

[63] Continuation of Ser. No. 88,697, Oct. 26, 1979, abandoned.

[51] Int. Cl.³ .............................................. G01N 33/54
[52] U.S. Cl. .................................... 436/500; 435/7; 436/532; 436/543; 436/804; 436/815; 436/823
[58] Field of Search ................. 23/230 B; 260/112 B, 260/121; 424/12; 435/7, 177, 188, 805; 436/500, 532, 543, 804, 815, 823

[56] References Cited

U.S. PATENT DOCUMENTS

| 3,879,262 | 4/1975 | Schuurs et al. | 435/7 |
| 3,940,475 | 5/1978 | Gross | 23/230 B |
| 3,951,748 | 4/1976 | Devlin | 435/7 |
| 4,001,583 | 1/1977 | Barrett | 435/7 |
| 4,017,597 | 4/1977 | Reynolds | 435/7 |
| 4,036,823 | 7/1977 | Soares | 424/12 |
| 4,053,459 | 10/1977 | Christenson | 260/112 B |
| 4,069,352 | 1/1978 | Parsons, Jr. | 424/12 |
| 4,070,246 | 1/1978 | Kennedy et al. | 435/177 |
| 4,092,116 | 5/1978 | Glaever | 435/7 |
| 4,100,268 | 7/1978 | Scherr | 260/112 B |
| 4,104,026 | 8/1978 | Brooker et al. | 424/12 |

Primary Examiner—Peter A. Hruskoci
Attorney, Agent, or Firm—Donald E. Nist

[57] ABSTRACT

The method comprises covalently binding an immunoreactive to a selected macromolecular carrier and then contacting the resulting hapten-carrier conjugate at a selected concentration in a liquid phase with a selected solid phase until a desired amount of the hapten-carrier conjugate is adsorbed to the surface of the solid phase. Unbound hapten-carrier conjugate is then separated from the solid phase, and the solid phase containing the bound hapten-carrier conjugate is recovered for use in quantitative immunoassays and the like. The solid phase can be, for example, surfaces of a test tube or microtiter well or the like. The method is simple and inexpensive and permits hapten assays of improved sensitivity.

7 Claims, 2 Drawing Figures

METHOD OF PASSIVELY ADSORBING IMMUNO-REACTIVE HAPTENS TO SOLID PHASES

This is a continuation of application Ser. No. 88,697, filed Oct. 26, 1979 now abandoned.

BACKGROUND OF THE INVENTION

1. Field of the Invention

The present invention generally relates to test materials and more particularly to a process for passively adsorbing immuno-reactive haptens to solid phases to permit immunoassays of increased sensitivity.

2. Prior Art

Haptens are classically measured by the competitive inhibition assay first described by Yalow and Berson (J. Clin. Invest. 39: 1157, 1960). This assay is a radioimmunoassay carried out by mixing a limiting amount of hapten-specific antibody with specified volumes of a sample containing an unknown amount of a hapten and a solution containing a known amount of the same hapten or an analog of the same hapten. Unlabeled and labeled haptens then compete for a limited number of antibody-binding sites. By separating the free and the antibody-bound labeled hapten into distinct fractions or phases and then measuring the amount of radioactivity in each of these two phases, one can quantitatively determine the amount of hapten in the sample being tested. Phase separation of the free hapten and the antibody-bound hapten can be accomplished by several methods which are currently in practice, including the use of species-specific antiglobulin to precipitate hapten-antibody complexes. Charcoal, ion exchange resins and various other types of solid phases have also been used to bind specific antibody.

The general methodologies and principles which are utilized in the radioisotope immunoassay methods employing phase separation to quantitate haptens have more recently also been applied to systems which employ reagents which are labeled with enzymes instead of radioisotopes. One such system is known as the enzyme-linked immunosorbent assay (ELISA), utilizing enzyme-hapten conjugates and a plastic solid phase to which hapten-specific antibody is adsorbed to effect phase separation. As in the case of radioimmunoassays, sample hapten and enzyme-labeled hapten compete for a limited number of antibody-combining sites on the solid phase. The amount of antibody-bound labeled hapten (which has an inverse relationship to the amount of hapten in the unknown sample) is determined by measuring the enzymatic activity of the solid phase.

A second system known as the enzyme multiplication immunoassay technique (EMIT) is similar to ELISA and certain radioimmunoassays in that enzyme-labeled hapten and sample hapten compete for a limited number of antibody-binding sites. However, EMIT does not require phase separation because the enzyme-hapten conjugate is prepared in such a manner that the enzyme will not react with substrate when antibody is bound to the enzyme-hapten conjugate. Consequently, EMIT specifically measures the amount of free or unbound enzyme-hapten conjugate.

There are few examples of hapten assays in which hapten itself is bound to a solid phase. One such example is the competetive enzyme-linked immunoassay (CELIA) described by Yorde et al. (Clin. Chem. 22:1372, 1976). In the CELIA system free hapten in an unknown sample and hapten covalently bound to a solid phase, such as Sepharose beads which are cross-linked dextran, compete for a limiting number of antibody (1st antibody) binding sites in solution. The quantity of hapten in the unknown sample is determined by measuring the amount of specific antibody bound to the solid phase. This measurement is accomplished by an enzymatic technique in which anti-globulin bound to 1st antibody and anti-enzyme-enzyme immune complex are added in sequence. The anti-globulin functions to bridge the bound hapten specific antibody with the anti-enzyme-enzyme immune complex which is the indicator system. One then measures the enzymatic activity of the solid phase in the presence of substrate.

A radioimmunoassay, similar to CELIA in principle, has been developed by Zollinger and Mandrell (Infect. and Immun. 18:424, 1977) to serotype bacteria. In this procedure, specific typing antibody is preincubated with a heterologous antigen (distinct form hapten) preparation. The reaction mixture is then added to microtiter wells passively coated with antigen homologous to the typing antisera. The amount of antibody bound to the solid phase (which has an inverse relationship with the degree of antigen similarity shared by the heterologous test antigen and the solid phase homologous antigen) is determined by adding a radio-labeled anti-globulin and then measuring the amount of label bound to the solid phase.

The primary advantage of using a solid-phase hapten, that is a hapten bound to a solid phase, as in the CELIA procedure, is that the sensitivity of the hapten assay can be increased dramatically by using labeled anti-globulin as the indicator system rather than labeled hapten.

The reason for enhanced sensitivity pertains to the increased number of enzyme labels that can be linked to antibody relative to hapten molecules. Thus, three to four enzyme molecules can be successfully linked to a single antibody, resulting in a conjugate that will demonstrate both antibody and enzymatic activity. In contrast, a single hapten molecule can be labeled with only one enzyme molecule. In reality, the final product is a population of enzyme molecules to which three or four hapten molecules are covalently bound.

If a solid phase hapten were employed in a competitive immunoassay, each hapten specific antibody reacting with the solid phase would result in either three to four to six to eight enzyme labels being bound, depending on whether labeled hapten specific or labeled second antibody were employed. In contrast, if one employed a hapten specific antibody solid phase in a competitive immunoassay, each solid phase antibody could react with two labeled hapten molecules resulting in only two enzyme labels being bound. Thus, the enhanced sensitivity of the immunoassays which employ solid phase hapten and labeled antibody is due to increased amplification of the serologic reaction by virtue of having more labels involved on a unit basis. Unfortunately, simple inexpensive methods of attaching haptens to solid phases have not heretofore existed. It therefore would be desirable to provide a simple, inexpensive, rapid, effective and reproducible method for attaching haptens to solid phases in order to improve the sensitivity of a hapten immunoassay,

SUMMARY OF THE INVENTION

The method of the present invention satisfies the foregoing needs. The method is substantially as set forth in the Abstract above. It is simple, inexpensive, rapid, reproducible and effective. It involves passively adsorbing immuno-reactive haptens to convenient solid phases such as the surface of tubes or microtiter wells through the use of selected macromolecular carriers for the haptens. In accordance with the method a hapten is first covalently bound to a selected macromolecular carrier for example by the use of a selected coupling agent, whereupon the resulting conjugate is diluted to a desired concentration and then in the liquid phase is placed into contact with a solid phase for adsorption of the hapten-carrier conjugate. The contacting is continued until the desired concentration of the conjugate is adsorbed onto the solid phase. The unbound conjugate and liquid are then removed from contact with the solid phase, and the solid phase containing the bound hapten-carrier conjugate is cleaned and is dried. It is now ready for use in immunoassays.

The macromolecular carrier can be, for example, bovine serum albumin, human serum albumin, egg albumin, polylysine or any other suitable carrier. Covalent binding is accomplished through the use of a coupling reagent, the nature of which is determined by the chemical group or groups on the hapten which are available for the covalent binding, and the particular carrier utilized. Typical coupling reagents include glutaraldehyde, carbodiimides, diisocyanates, (O-carboxymethy-) hydroxylamines, anhydrides, diazonium compounds and dihalogenated dinitrobenzenes.

Once the conjugate is formed, it usually is diluted in a suitable coating buffer, for example, a mixture of sodium carbonate and sodium bicarbonate having a pH of about 9.6. A specified volume of this solution containing the conjugate is then added to assay tubes, microtiter wells or another container of choice which can function as as solid phase. Such containers are usually fabricated of polystyrene, polyethylene or another conjugate-adsorbent plastic. Once the conjugate is adsorbed from the liquid phase to the solid phase and the unbound conjugate is removed with the liquid buffer, the solid phase can be washed, dried and stored for future use in performing an immunoassay test. Further details of the present invention are set forth in the following detailed description.

DETAILED DESCRIPTION

Figure 1:
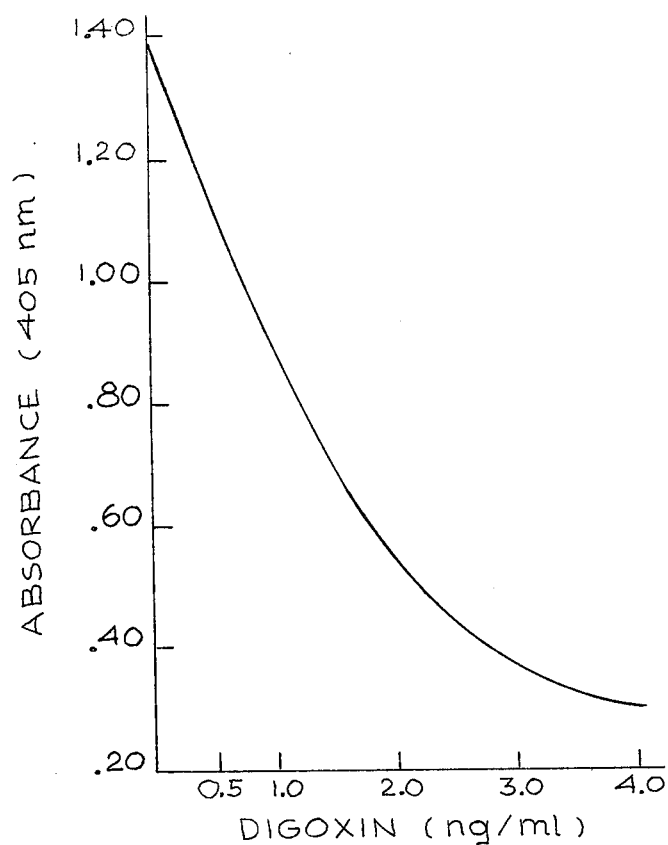
Figure 2:
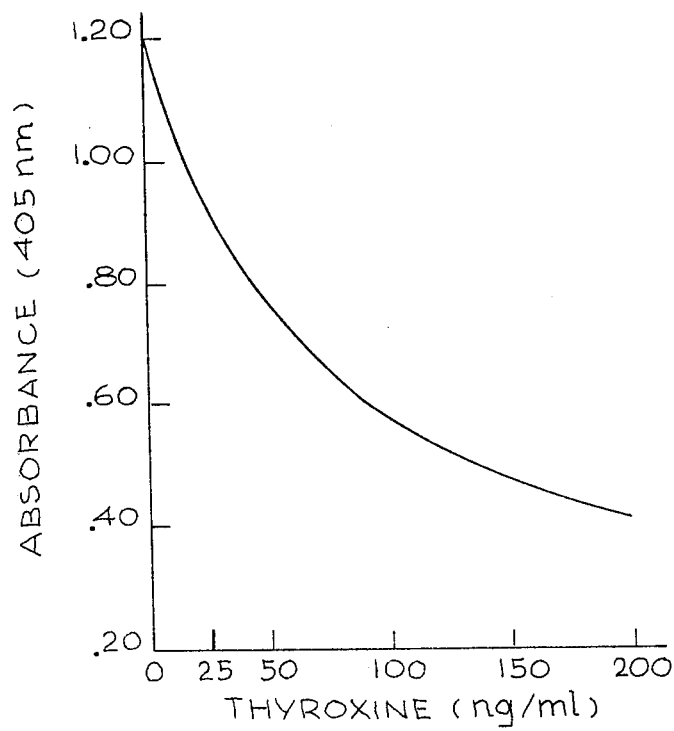

In accordance with the method of the present invention a selected hapten which will be assayed is covalently bound to an appropriate macromolecular carrier. The hapten may be any one or more of a wide variety of materials, for example, drugs, animal and plant hormones, antibiotics, pesticides and the like. The macromolecular carrier may be any suitable material to which the hapten can be conveniently covalently bound by a coupling reagent. As previously indicated, typical macromolecular carriers employed in the present method comprises bovine serum albumin, human serum albumin, egg albumin and polylysine, as well as the following typical carriers, immunoglobulin, lipid A, collagen and the like. A coupling reagent is normally used to effect the covalent binding between the hapten and the macromolecular carrier. In addition to the coupling reagents previously listed, the following typical coupling reagents can also be used: hydrazides, azides, cyanogen bromide, N,N-o-phenylenedimaleimide, m-maleimidobenzoyl-N-hydroxysuccinimide ester and the like. The selection of the coupling reagent will depend upon the particular hapten and macromolecular carrier. Typical examples of coupling reagents which are used for selected haptens and macromolecular carriers are set forth in the table below.

TABLE

| SAMPLE NO. | HAPTEN | MACROMOLECULAR CARRIER | COUPLING REAGENT |
|---|---|---|---|
| 1 | gentamicin | bovine serum albumin | glutaraldehyde |
| 2 | digoxin | human serum albumin | periodate & sodium borohydride |
| 3 | thyroxine | bovine serum albumin | glutaraldehyde |
| 4 | triiodothyronine | bovine serum albumin | glutaraldehyde |

In bringing about the covalent binding, normally the coupling reagent is added to a solution or mixture of the hapten and/or macromolecular carrier, the concentration of the coupling reagent varying with the particular system involved. As a typical example, in the sample listed as No. 1 in the table above, the coupling reagent is initially mixed with the macromolecular carrier to provide a concentration of coupling reagent to carrier of about 2:1 by weight, whereupon after a 3-hour incubation period at room temperature, the solution is chromatographed on a column of cross-linked dextran (with a molecular weight exclusive limit of 2500) and the first 20 ml after the void volume are collected. To the resulting collected mixture is added 200 mg of hapten, whereupon the resulting mixture is incubated for about 20 hours at room temperature with stirring, and then 500 mg of glycine is added. The final mixture is incubated an additional two hours at room temperature, after which this conjugate solution is dialyzed for about three days against distilled water at room temperature and then lyophilized to provide a finished carrier-hapten conjugate.

After the carrier-hapten conjugate is prepared in accordance with the present method as described above, it is diluted in a suitable buffer, such as carbonate-bicarbonate, pH 9.6, to a selected concentration, for example, about 100 ng/ml. It will be understood that other buffers can be used, for example, glycine buffer, pH 9.5 and that other dilutions can be made, for example, 50 ng/ml. It is preferred that the conjugate in the liquid phase be in a concentration range of about 10 ng/ml to about 200 ng/ml when contacting the solid phase. Such solid phase may be any suitable material capable of absorbing the conjugate within a reasonable amount of time. Preferably, however, a standard plastic test tube, microtiter well or other container of choice, fabricated for example of polystyrene, polyethylene, or another plastic such as polyvinyl acetate or polyvinyl chloride is utilized because it is inexpensive, effects adsorption without about 24 hours under normal conditions and can be easily dried and stored for future use. A typical substrate will comprise a microtiter plate containing a plurality of spaced wells, the plate being fabricated or polystyrene and capable of absorbing the conjugate within about 15 to 24 hours when the conjugate in the buffer is disposed in the wells and incubated therein at about 4° C. to about 25° C. over the contact period. During this incubation period a uniform amount of the hapten-carrier conjugate will absorb directly to the surface of the microtiter wells within which the conjugate-containing liquid is disposed and become bound tightly thereto. When a desired concentration of the conjugate is absorbed to the microtiter well surface, the concentration depending upon the incubation time, the solid phase can then be washed free of unbound conjugate. The washing can be effected with any suitable solution, for example, phosphate-buffered saline solution fortified with a surfactant such as TWEEN 20 or TWEEN 80, a polyoxyethylene derivative sold under that U.S. registered mark which is owned by Atlas Chemical Industries, Inc. Alternatively, distilled water could be used. After several washings to assure that no unbound conjugate is left in contact with the solid phase, the solid phase can either be blotted dry, air dried or lyophilized and then stored dry for future use. The following specific two examples further illustrate further features of the present invention.

EXAMPLE I

(a) Preparation of Digoxin—Human Serum Albumin Conjugate.

A human serum albumin-digoxin conjugate was prepared by a periodate oxidation procedure described previously by Smith et al. (Biochemistry, 9: 331–337, 1970). Typically 436 mg of digoxin was suspended in 20 ml of absolute ethanol at room temperature to which was added dropwise with stirring 20 ml of 0.1 M sodium metaperiodate. After 25 minutes, 0.6 ml of 1.0 M ethylene glycol was added. Following a five minute incubation period, the reaction mixture was added dropwise with stirring to 560 mg of human serum albumin dissolved in 20 ml of distilled $H_2O$ (pH previously adjusted to 9.5 with 5% $K_2CO_3$). This reaction mixture was maintained in the 9.0–9.5 pH range by the dropwise addition of $K_2CO_3$. After 45 minutes, 0.3 g of sodium borohydride dissolved in 20 ml of distilled $H_2O$ was added. Following a 3-hour incubation period, 1.0 M formic acid was added dropwise to lower the pH to 6.5. One hour later, the pH was raised to 8.5 by the addition of 1.0 M $NH_4OH$. The reaction mixture was then dialyzed overnight against cold running tap water. After 24 hours, the pH was lowered to 4.5 by the dropwise addition of 0.1 N HCl. The reaction mixture was left at room temperature for one hour and then placed at 4° C. for four hours. The precipitated protein was collected by centrifugation at 1000X g for one hour at 4° C. After discarding the supernatant, the precipitate was dissolved in a minimal amount of 0.19 M $NaHCO_3$. This solution was then dialyzed against cold running tap water for four days and then lyophilized as human serum albumin-digoxin conjugate (HSA-D).

(b) Coating Polystyrene Microtiter Plates with HSA-D.

HSA-D was dissolved in 0.015 M carbonate-bicarbonate buffer (pH 9.5) at a concentration of 100 ng/ml. The wells of the plates were filled with 250 µl of the HSA-D solution, after which the plates were placed in a 4° C. humid chamber and incubated overnight. On the following day, the liquid content of the wells was dumped out and the plates lyophilized for two hours. After lyophilization, the plates were packaged and sealed along with a dessicant in plastic bags for future use.

(c) Competitive Enzyme-Linked Immunosorbent Assay for Digoxin Using HSA-D Coated Microtiter Plates.

In a typical assay, 50 µl of each serum sample was added to duplicate HSA-D coated wells to which was then added µl of an appropriate dilution of rabbit anti-digoxin prepared in phosphate buffered saline with Tween (PBS-Tween). After a 30-minute incubation period, the wells were washed three times with PBS-Tween and then filled with 250 µl of an appropriate dilution of alkaline phosphate conjugated sheep anti-rabbit IgG. Following a 30-minute incubation period at room temperature, unreacted conjugate was removed by washing the wells with PBS-Tween three times. The serologic reaction was then developed by adding 250 µl of enzyme substrate (1.0 mg p-nitrophenyl phosphate/ml of pH 9.8 diethanolamine buffer) to each well and incubating at room temperature for 45 minutes. The enzymatic reaction was stopped at this point by the addition of 50 µl of 3 N NaOH to each well. The reaction was measured spectrophotometrically by determining the absorbance value for the contents in each well at 405 nm. The mean value for each of the digoxin standards was computed and used to construct the standard curve. The amount of digoxin in the unknown samples was determined from that standard curve.

EXAMPLE II

(a) Preparation of Thyroxin-Bovine Serum Albumin Conjugate.

A bovine serum albumin-thyroxin conjugate was prepared by a procedure which employed glutaraldehyde coupling reagent. The conjugation was initiated by mixing equal volumes of a 0.009 mM solution of bovine serum albumin (BSA) containing 9.02 M PBS, pH 7.6 and a 0.125 mM solution of thyroxin (0.01 M PBS, pH adjusted to 10 with 1 N NaOH). After mixing at room temperature for two hours, a 25% solution of gluteraldehyde was added to a final concentration of 0.2%. This reaction mixture was stirred gently at room temperature for two hours and then dialyzed for three days against a minimum of 100 volumes of 0.01 M PBS (pH 7.6) changed at 24-hour intervals. The conjugation protocol was completed by a final 24-hour dialysis against 0.05 M Tris buffer at pH 8.0. The final product was stored at −20° C. for future use.

(b) Coating Polystyrene Cuvettes

BSA-thyroxin was dissolved in 0.015 M carbonate bicarbonate buffer (pH 9.5) at a concentration of 200 ng/ml. The wells of the plates were filled with 250 µl of the BSA-thyroxin solution, after which the plates were placed in a 4° C. humid chamber and incubated overnight. On the following day, the liquid contents of the wells were dumped out and the plates lyophilized for two hours. After lyophilization, the plates were packaged and sealed along with a dessicant in plastic bags for future use.

(c) Competitive Enzyme-Linked Immunosorbent Assay for Thyroxin Using BSA-Thyroxin Coated Microtiter Plates.

In a typical assay, 10 µl of each unknown serum sample was added to duplicate BSA-Thyroxin coated wells to which 250 µl of an appropriate dilution of rabbit anti-thyroxine prepared in PBS-Tween. After a 30-minute incubation period, the wells were washed three times with PBS-Tween and then filled with 250 μl of an appropriate dilution of alkaline phosphates conjugated sheep anti-rabbit IgG. Following a 30-minute incubation period at room temperature, unreacted conjugate was removed by washing the wells with PBS-Tween three times. The serologic reaction was then developed by adding 250 μl of enzyme substrate (1.0 mg p-nitrophenyl phosphate/ml of pH 9.8 diethanolamine buffer) to each well and incubating at room temperature for 45 minutes. The enzymatic reaction was stopped at this point by the addition of 50 μl of 3 N NaOH to each well. The reaction was measured spectrophotometrically be determining the absorbance value for the contents in each well at 405 nm. The mean value for each of the thyroxin standards was computed and used to construct a standard curve. The amount of thyroxin in the unknown samples was determined from that standard curve.

Examples I and II set forth above clearly illustrate that the method of the present invention is simple, inexpensive and effective for passively adsorbing immuno-reactive haptens to solid phases. The resulting conjugate-bound solid-phases are useful in immunoassays of various types. The sensitivity of such assays is increased over other types of assays because of the use of the hapten bound to the solid phase.

It will be understood that various modifications, changes, alterations and additions can be made in the method of the present invention, its steps and parameters. All such modifications, changes, alterations and additions as are within the scope of the appended claims form part of the present invention.

What is claimed is:

1. A method of readily adsorbing immuno-reactive hapten to a solid phase for an immuno-assay, which hapten otherwise would not readily adsorb to said solid phase and retain its immuno-reactivity, which method retains said immuno-reactivity and comprises:
   a. covalently binding an immuno-reactive hapten selected from the group consisting of digoxin, thyroxin, gentamicin, and triiodothyronine to a macromolecular carrier selected from the group consisting of bovine serum albumin, and human serum albumin through the use of a coupled agent selected from the group consisting of glutaraldehyde, and periodate with sodium borohydride;
   b. contacting the resulting hapten-carrier conjugate with a solid phase selected from the group consisting of polystyrene, and polyvinyl acetate until a desired concentration of said hapten-carrier conjugate is adsorbed to the surface of said solid phase; and,
   c. thereafter removing unbound hapten-carrier conjugate from said solid phase and recovering said solid phase containing said bound hapten-carrier conjugate.

2. The method of claim 1 wherein said hapten-carrier conjugate is in a liquid phase when said contacting with said solid phase is initiated.

3. The method of claim 2 wherein said hapten-carrier conjugate is diluted to a desired concentration with a liquid diluent and then contacted with said solid phase while still in said diluent.

4. The method of claim 1 wherein said hapten comprises digoxin, wherein said macromolecular carrier comprises human serum albumin, wherein said coupling reagent comprises periodate and sodium borohydride, and wherein said solid phase comprises polystyrene.

5. The method of claim 1 wherein said hapten comprises thyroxin, wherein said macromolecular carrier comprises bovine serum albumin, wherein said coupling reagent comprises glutaraldehyde, and wherein said solid phase comprises polystyrene.

6. The method of claim 1 wherein said hapten comprises gentamicin, wherein said macromolecular carrier comprises bovine serum albumin, wherein said coupling reagent comprises glutaraldehyde, and wherein said solid phase comprises polystyrene.

7. The method of claim 1 wherein said hapten comprises triiodothyronine, wherein said macromolecular carrier comprises bovine serum albumin, wherein said coupling reagent comprises gluta aldehyde, and wherein said solid phase comprises polyvinyl acetate.

* * * * *